United States Patent
Xiao et al.

(10) Patent No.: US 10,743,980 B2
(45) Date of Patent: Aug. 18, 2020

(54) LUMEN WOVEN SUPPORT

(71) Applicant: Lifetech Scientific (Shenzhen) Co., Ltd., Shenzhen (CN)

(72) Inventors: Benhao Xiao, Shenzhen (CN); Qin Wang, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 32 days.

(21) Appl. No.: 15/770,594

(22) PCT Filed: Jun. 8, 2016

(86) PCT No.: PCT/CN2016/085185
§ 371 (c)(1),
(2) Date: Apr. 24, 2018

(87) PCT Pub. No.: WO2017/071231
PCT Pub. Date: May 4, 2017

(65) Prior Publication Data
US 2019/0053887 A1      Feb. 21, 2019

(30) Foreign Application Priority Data

Oct. 26, 2015    (CN) .......................... 2015 1 0703190

(51) Int. Cl.
| | | |
|---|---|---|
| *A61F 2/07* | (2013.01) | |
| *A61F 2/90* | (2013.01) | |
| *A61F 2/82* | (2013.01) | |

(52) U.S. Cl.
CPC .................. *A61F 2/07* (2013.01); *A61F 2/82* (2013.01); *A61F 2/90* (2013.01);
(Continued)

(58) Field of Classification Search
CPC .... A61F 2/1613; A61F 2/1648; A61F 2/1635; A61F 2/1694; A61F 2002/1681
(Continued)

(56) References Cited

U.S. PATENT DOCUMENTS

| | | |
|---|---|---|
| 6,221,100 B1 | 4/2001 | Strecker |
| 2005/0137680 A1 | 6/2005 | Ortiz et al. |

(Continued)

FOREIGN PATENT DOCUMENTS

| | | |
|---|---|---|
| CN | 101006947 A | 8/2007 |
| CN | 105250058 A | 1/2016 |

(Continued)

OTHER PUBLICATIONS

International Search Report dated Sep. 12, 2016 for corresponding PCT application No. PCT/CN2016/085185.
(Continued)

*Primary Examiner* — Christopher D. Prone
*Assistant Examiner* — Tiffany P Shipmon
(74) *Attorney, Agent, or Firm* — Raymond Sun

(57) ABSTRACT

A lumen woven support (100), comprising a netted tube body (10) woven by weaving filaments (1), wherein the netted tube body (10) comprises a first portion (110) and a second portion (120) along an axial direction; the netted tube body (10) further comprises a plurality of first hooked and wound knots (140), at least two weaving filaments (1) from one end of the second portion (120) are hooked and wound to each other in the axial direction of the netted tube body (10) to form a first hooked and wound knot (140) and are then separated, and all the weaving filaments (1) constituting the first hooked and wound knots (140) are woven to form the first portion (110); and the mesh density of the first portion (110) is smaller than that of the second portion (120). In the above-mentioned lumen woven support (100), since (Continued)

the mesh density of the first portion (110) is smaller than that of the second portion (120), the radial supporting force of the first portion (110) is reduced, and the stimulation to a normal lumen wall caused by the first portion (110) is reduced, thereby lowering a risk of restenosis. In addition, the first portion (110) has a good flexibility, the second portion (120) has a greater radial supporting force so as to provide sufficient anchoring, and therefore, the above-mentioned lumen woven support (100) is applicable to practical implantation.

10 Claims, 3 Drawing Sheets

(52) U.S. Cl.
CPC .............. *A61F 2220/0016* (2013.01); *A61F 2220/0075* (2013.01); *A61F 2230/0067* (2013.01); *A61F 2240/001* (2013.01); *A61F 2250/0017* (2013.01); *A61F 2250/0018* (2013.01); *A61F 2250/0039* (2013.01)

(58) Field of Classification Search
USPC ............... 623/1.13, 1.5, 1.51, 1.53, 1.54
See application file for complete search history.

(56) References Cited

U.S. PATENT DOCUMENTS

2010/0211154 A1    8/2010   Murayama et al.
2017/0304093 A1*   10/2017   During ................ A61F 2/90

FOREIGN PATENT DOCUMENTS

| CN | 205198216 U | 5/2016 |
|---|---|---|
| WO | WO2011/032720 A1 | 3/2011 |
| WO | WO2012/120953 A1 | 9/2012 |

OTHER PUBLICATIONS

Office Action dated Nov. 28, 2016 in corresponding China application No. 201510703190.8.

\* cited by examiner

LUMEN WOVEN SUPPORT

TECHNICAL FIELD

The present application relates to the technical field of medical instruments, and more particularly relates to an endoluminal braided stent graft.

BACKGROUND ART

An endoluminal braided stent graft has a radial compression state and a radial expansion state when used. During use, the endoluminal braided stent graft in the radial compression state is delivered to a diseased position in a lumen of a human body through a delivery device, and then is released. It automatically expands to be unfolded or it is unfolded in a mechanical way (for example, it is unfolded through balloon dilatation) and is attached to the lumen wall to support the lumen wall on the basis of its radial supporting force, thereby achieving an effect of expanding a diseased lumen wall to maintain smoothness of the lumen.

In the prior art, the endoluminal braided stent graft generally includes a meshed tubular body woven by at least one weaving filament. The meshed tubular body has a uniform woven structure. However, after the endoluminal braided stent graft is implanted into the human body, an open end portion is generally attached to a normal lumen wall, and a support main body portion is attached to a diseased region of the lumen. In order to guarantee effective expansion of a diseased lumen, the support is required to have a greater radial supporting force so as to provide sufficient anchoring, but the greater radial supporting force may generate greater stimulation to a normal lumen; for example, the open end portion of the support would generate greater stimulation on the normal lumen, and the greater stimulation would increase organ reaction of an organ to external foreign matters and increase a risk of restenosis. In addition, shapes of lumens of the human body have an obvious individual difference; for a bent lumen portion, the support is required to have a better flexibility, but for a smooth lumen portion, the support is required to have the greater radial supporting force so as to provide the sufficient anchoring. In conclusion, the support having a uniform integrated woven structure cannot be applicable to practical implantation.

SUMMARY OF THE INVENTION

In view of the above, it is necessary to provide an endoluminal braided stent graft which can be applicable for practical implantation, to address the problem that the conventional endoluminal braided stent graft cannot be applicable to all practical implantations.

The present application provides an endoluminal braided stent graft, including a meshed tubular body woven by weaving filaments. The meshed tubular body includes a first portion and a second portion along an axial direction; the meshed tubular body further includes a plurality of first hooked and wound knots; at least two weaving filaments from one end of the second portion are hooked and wound to each other in the axial direction of the meshed tubular body to form one of the first hooked and wound knots and are then separated, and all the weaving filaments constituting the first hooked and wound knots are woven to form the first portion; and the mesh density of the first portion is smaller than that of the second portion.

According to the endoluminal braided stent graft provided by an embodiment of the present application, the plurality of first hooked and wound knots are uniformly distributed in the circumferential direction of the meshed tubular body.

According to the endoluminal braided stent graft provided by an embodiment of the present application, the meshed tubular body includes a plurality of second portions which are spaced arrayed along the axial direction, and every two adjacent second portions are connected with each other through the plurality of first hooked and wound knots.

According to the endoluminal braided stent graft provided by an embodiment of the present application, the meshed tubular body further includes a plurality of second hooked and wound knots and a third portion, and the third portion and the first portion are respectively located at two ends of the second portion; at least two filaments from the other end of the second portion are hooked and wound to each other to form one of the second hooked and wound knots and are then separated; and the filaments of all the second hooked and wound knots are woven to form the third portion.

According to the endoluminal braided stent graft provided by an embodiment of the present application, the mesh density of the third portion is different from that of the second portion.

According to the endoluminal braided stent graft provided by an embodiment of the present application, the plurality of second hooked and wound knots are uniformly distributed in the circumferential direction of the meshed tubular body.

According to the endoluminal braided stent graft provided by an embodiment of the present application, the mesh density of the first portion is the same as that of the third portion.

According to the endoluminal braided stent graft provided by an embodiment of the present application, the meshed tubular body includes a plurality of third portions which are spaced arrayed along the axial direction, and every two adjacent third portions are connected with each other through the multiple second hooked and wound knots.

According to the endoluminal braided stent graft provided by an embodiment of the present application, the first portion includes a conical open end portion, and the radius length of the conical open end portion is gradually increased from one side closer to the second portion to another side further away from the second portion.

According to the endoluminal braided stent graft provided by an embodiment of the present application, an opening angle of the conical open end portion is 45 to 120 degrees.

According to the endoluminal braided stent graft provided by an embodiment of the present application, at least two weaving filaments in each first hooked and wound knot are hooked and wound to each other once, or at least two weaving filaments in each first hooked and wound knot are continuously hooked and wound to each other at least twice.

When the meshed tubular body includes a plurality of the second hooked and wound knots, two of the weaving filaments in the second hooked and wound knots are hooked and wound once, or two of the weaving filaments in the second hooked and wound knots are continuously hooked and wound at least twice.

In the above-mentioned endoluminal braided stent graft, since the mesh density of the first portion is smaller than that of the second portion, a radial supporting force of the first portion is reduced, and stimulation to a normal lumen wall caused by the first portion is reduced, thereby lowering the risk of restenosis. In addition, the first portion has a good flexibility, the second portion with a greater radial supporting force can provide sufficient anchoring, and therefore, the above-mentioned endoluminal braided stent graft is applicable to practical clinical implantation.

Since at least two weaving filaments from one end of the second portion are hooked and wound to each other to form one of the first hooked and wound knots and are then separated, and all the weaving filaments constituting the first hooked and wound knots are woven to form the first portion, in other words, the first portion, the multiple first hooked and wound knots and the second portion are all woven by the same weaving filaments, the quantity of the weaving filaments in each portion is equal, and all the portions may be integrally woven.

DETAILED DESCRIPTION OF THE INVENTION

For the purpose of making objects, technical schemes and advantages of the present application more clear, detailed description will be further made to the present application in conjunction with corresponding drawings and embodiments. Obviously, the described specific embodiments are merely an explanation of the present application, but do not limit the present application.

Unless otherwise defined, all technical and scientific terms used in the text have the same meanings of general understandings of a person skilled in the art of the present application. Terms used in the specification of the present application in the text are intended to describe the specific embodiments, but not to limit the present application. The term "and/or" used in the text includes any and all combinations consisting of one or multiple relevant listed items.

Figure 1:
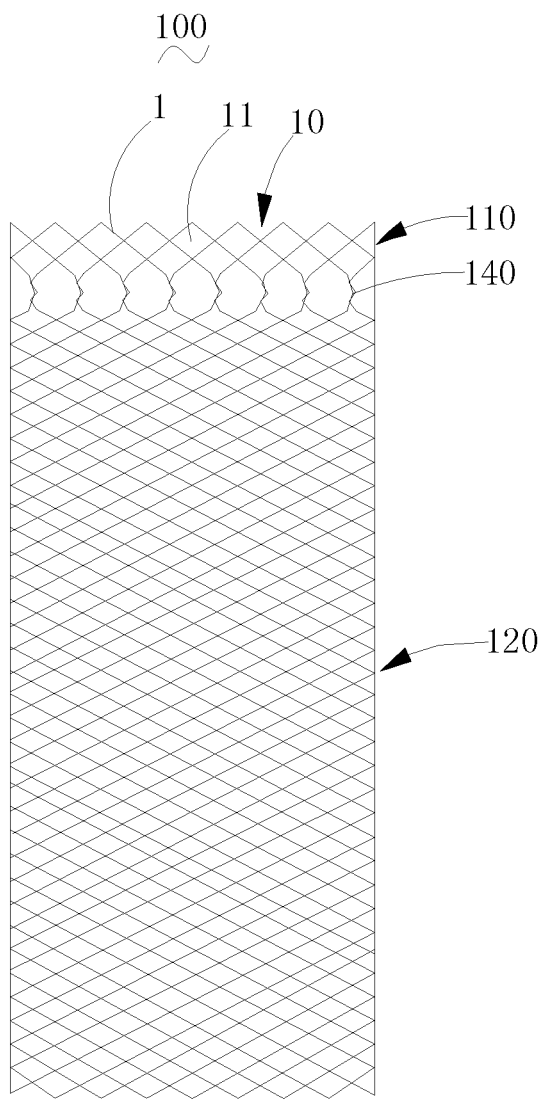
FIG. 1 is a structural schematic diagram of an endoluminal braided stent graft provided by a first embodiment of the present application.

With reference to FIG. 1, an endoluminal braided stent graft 100 provided by one embodiment of the present application includes a meshed tubular body 10 woven by weaving filaments 1. The meshed tubular body 10 has a number of woven meshes 11 and includes a first portion 110, a number of first hooked and wound knots 140 and a second portion 120 along an axial direction; and each first hooked and wound knot 140 is formed by mutually hooking and winding at least two weaving filaments 1 along the axial direction. Each hooked and wound knot is a "twisted" structure formed by spirally twisting one weaving filament along the lengthwise direction of another weaving filament or the lengthwise directions of multiple weaving filaments. The hooked and wound knots may be basically parallel to the axial direction of the meshed tubular body 10, or not parallel to the axial direction of the meshed tubular body 10.

Every two adjacent hooked and wound knots may be parallel to each other, or not parallel to each other. The first portion 110 is connected with the second portion 120 through the multiple hooked and wound knots 140; the mesh density of the first portion 110 is smaller than that of the second portion 120, and the lengths of the multiple first hooked and wound knots 140 may be either equal or not equal. Connecting lines of the end portions of proximal ends and/or distal ends of all the first hooked and wound knots 140 may be located in a plane perpendicular to the axial direction of the meshed tubular body 10. In the specific embodiment, the multiple first hooked and wound knots 140 are uniformly distributed along the circumferential direction of the meshed tubular body 10, and each hooked and wound knot 140 is basically parallel to the axial direction of the meshed tubular body 10. At least two first hooked and wound knots 140 are provided. It should be known that a proper number of the first hooked and wound knots 140 may be selected as required, for example, 3 to 12 hooked and wound knots are selected, and no more detailed description is given here.

In the above-mentioned endoluminal braided stent graft, the first portion 110 and the second portion 120 which are connected with each other through the first hooked and wound knots 140 are two independent woven bodies formed by hooking and winding the filaments, and their weaving parameters (such as weaving angles and directions) are not limited to each other or restrained by each other, and the weaving parameters of the first portion 110 and the second portion 120 may be independently adjusted as required, thereby the first portion 110 and the second portion 120 may have different weaving parameters, and correspondingly, the mesh densities in the two woven bodies may also be different. The mesh density here is the number of woven meshes within a unit area. If the mesh density of one woven body is smaller, the woven body has a better flexibility and a smaller radial supporting force, and vice versa.

The meshed tubular body 10 is an axial cavity having a proximal end opening and a distal end opening. In the present application, body fluid (such as blood) is defined to flow from the proximal end to the distal end, and after the stent is implanted into a lumen, the cavity becomes a new body fluid channel, for example, after the stent is implanted into a blood vessel, the cavity becomes a new blood flow channel. The meshed tubular body 10 is formed by weaving at least one weaving filament 1, for example, it may be either formed by weaving one weaving filament in a reciprocating manner, or formed by mutually matching a plurality of weaving filaments in a crossing manner; no further description is provided herein, and all are described as multiple weaving filaments. The weaving filaments 1 are either nickel-titanium filaments or weaving filaments made of other biological materials.

With reference to FIG. 1, if the first portion 110 includes an open end portion, this portion is attached to a normal lumen wall after the stent is implanted, and the second portion 120 is attached to a diseased lumen wall. The first portion 110 has a sparser mesh density than the second portion 120; therefore, the first portion 110 has smaller radial supporting force, which reduces stimulation to the normal lumen wall, weakens organ reaction of an organ to external foreign matters, and lowers the risk of restenosis. In addition, the second portion 120 with larger mesh density still can provide a sufficient radial supporting force to guarantee anchoring of the stent in the lumen. Or, in case of implantation into a bent lumen portion, the first portion 110 has the better flexibility due to its smaller mesh density, and at a smooth lumen portion, the second portion 120 can provide a greater radial supporting force to guarantee sufficient anchoring.

The meshed tubular body 10 may be woven in an axially spiral weaving method. The crossed weaving filaments 1 are staggered in a manner of one pressing one or one pressing multiple during weaving, thus finally forming a tubular woven structure with the meshes 11. Of course, the crossed weaving filaments may be staggered in any other proper ways. The weaving method of the present application is not limited to the axially spiral weaving method, and any proper weaving method may be selected as required; for example, an axially Z-shaped weaving method and the like. It should be known that as one weaving filament is crossed in a reciprocating manner or different weaving filaments are crossed, no further description is provided here, but all the weaving methods are crossing or staggering or intersecting or weaving of one weaving filament and another weaving filament or multiple weaving filaments.

At least two weaving filaments from one end of the second portion 120 are hooked and wound to each other to form a first hooked and wound knot 140 and are then separated, and all the weaving filaments constituting the first hooked and wound knots 140 are woven to form the first portion 110. In other words, each first hooked and wound knot 140 is formed by hooking and winding at least two weaving filaments with different winding directions (for example the winding directions are opposite) from the second portion 120, and all the weaving filaments weaving the second portion are all used for weaving the first hooked and wound knots 140. For example, the hooked wound knots may be formed by hooking and winding only two weaving filaments, or formed by hooking and winding more than two weaving filaments; in other words, any one weaving filament in each hooked and wound knot is hooked and wound to at least one other weaving filament in the hooked and wound knot. Two weaving filaments in each hooked and wound knot may be hooked and wound to each other in various ways; for example, the two weaving filaments in each hooked and wound knot may be hooked and wound once, or continuously hooked and wound for multiple times.

Figure 2:
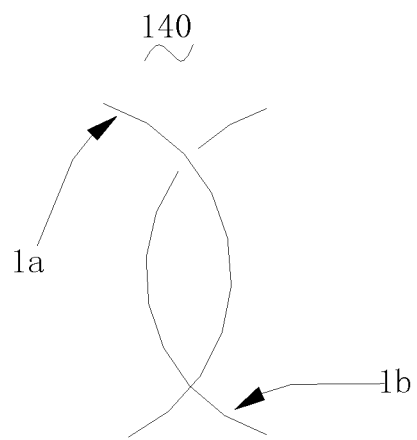
FIG. 2 is a schematic diagram of a hooking and winding mode of hooked and wound knots of the endoluminal braided stent graft in FIG. 1.
Figure 3:
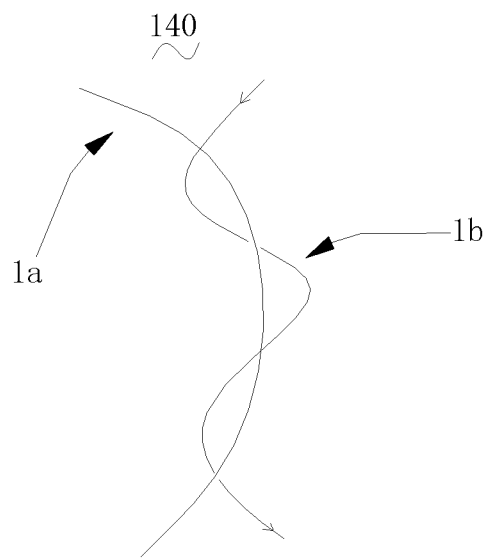
FIG. 3 is a schematic diagram of another hooking and winding mode of hooked and wound knots.

With reference to FIG. 2, when two weaving filaments 1a and 1b are hooked and wound in a crossing manner, one weaving filament (for example the weaving filament 1b) is hooked to the other weaving filament (for example the weaving filament 1a) and is then wound from one side to the other side to form hooking and winding. With reference to FIG. 3, when two weaving filaments 1a and 1b are hooked and wound in a crossing manner, one weaving filament (for example the weaving filament 1b) is repeatedly hooked to the other weaving filament (for example the weaving filament 1a) for multiple times to form continuous hooking and winding for multiple times. By adjusting the number of times of continuous hooking and winding, the length of each hooked and wound knot is adjusted. For example, the winding length of each hooked and wound knot formed by hooking and winding the weaving filaments for multiple times may be adjusted to be 2+/−0.5 mm. Of course, it is not limited to this value, and the length may be adjusted according to an actual requirement. It should be known that illustrated loose-looking hooking and winding between the weaving filaments as shown in FIG. 2 and FIG. 3 is to facilitate viewing of the Figures. A person skilled in the art may adopt a close hooking and winding method where all the weaving filaments are twisted into one. In particular, for the manner where the weaving filaments are hooked and wound for multiple times in FIG. 3, after closely hooked and winding for multiple times, the hooked and wound weaving filaments are basically relatively fixed and are hard to move relative to each other.

In the hooking and winding process, the weaving directions of two weaving filaments are changed, so that two weaving filaments constituting each first hooked and wound knot 140 do not restrict each other or constrict each other after being separated, and proper weaving parameters or weaving methods may be selected for weaving filaments on two sides according to a clinical requirement. Correspondingly, the weaving parameters or weaving methods of the first portion 110 and the second portion 120 which are connected through the first hooked and wound knots 140 are independently selected; for example, a weaving angle of the first portion 110 and a weaving angle of the second portion 120 are independently set, so as to enable the woven mesh density of the first portion 110 to be different from that of the second portion 120.

Figure 4:
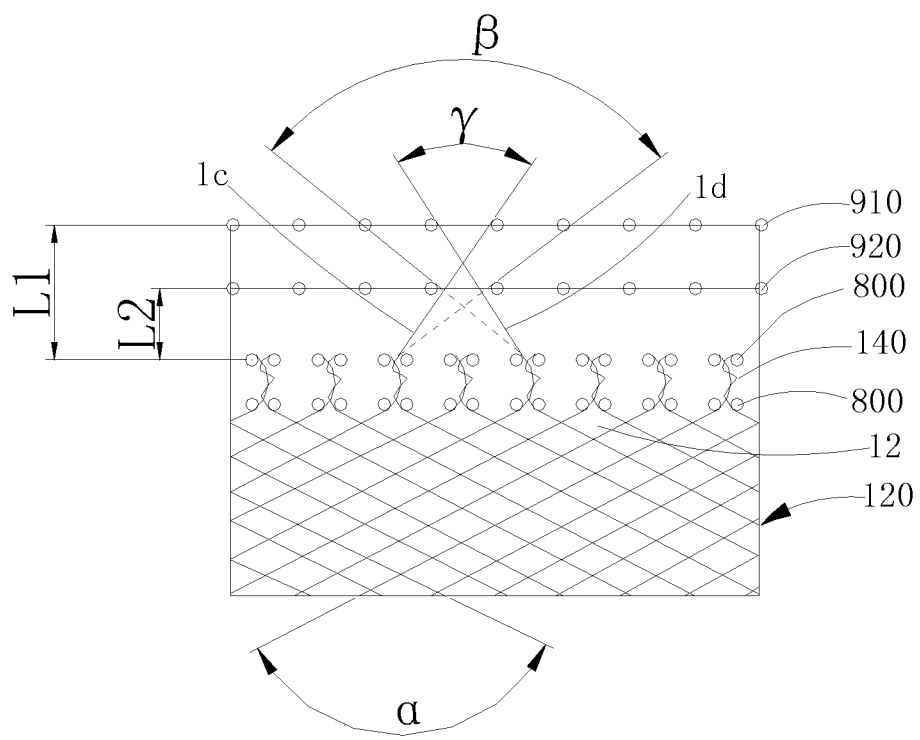
FIG. 4 is a schematic diagram of a weaving principle of a first portion of the endoluminal braided stent graft in FIG. 1.

With reference to FIG. 4, two weaving filaments of the second portion 120 are woven at a weaving angle α to form a woven grid 12 and then are hooked and wound to each other to form the first hooked and wound knot 140; and relative to the state before hooking, the two weaving filaments are independent of each other after hooking, and a proper weaving method may be selected again according to a clinical requirement; for example, a proper weaving angle is selected to weave the first portion 110. At the moment, all the weaving filaments weaving the second portion 120 are used for weaving all the first hooked and wound knots 140, and all the weaving filaments weaving all the first hooked and wound knots 140 are used for weaving the entire first portion 110.

For example, a mandrel (not shown in the figure) is adopted to weave the meshed tubular body. A number of pins are arranged on the mandrel. FIG. 4 shows a first group of pins 800 for forming the hooked and wound knots and a second group of pins 910 or 920 for weaving the first portion 110, and the first group of pins 800 is closely adjacent to the second group of pins 910 or 920. Weaving filaments 1c and 1d are respectively hooked and wound through two pins in the first group of pins 800 and are then crossed, so as to weave the first portion 110 at a weaving angle β. The size of β is related to the pins selected from the second group of pins 910 or 920. The weaving filament 1c is taken for an example: if a relative distance along the circumferential direction between the filament hanging rods in the first group of pins 800 and the pins in the closely adjacent second group of pins 910 or 920 is smaller, the weaving angle β is smaller, and the correspondingly formed woven mesh density is smaller. Or, the weaving angle is also adjusted via adjusting a relatively axial distance between the first group of pins 800 and the closely adjacent second group of pins 910 or 920. If the relatively axial distance between the first group of pins 800 and the second group of pins 910 or 920 is adjusted from L2 to relatively long L1, under a condition that L1 is equal to the relative distance along the circumferential direction from the pin of the first group of pins 800, a weaving angle γ formed by adoption of the pin 920 (corresponding to L2) is smaller than the weaving angle β formed by adoption of the pin 910 (corresponding to L1), that is to say, the relatively axial distance is larger, and the weaving angle is smaller.

From the above, in the meshed tubular body of the present application, after being hooked and wound to each other, two weaving filaments of the first portion 110 become weaving filaments of the second portion 120, or after being hooked and wound, two weaving filaments of the second portion 120 become weaving filaments of the first portion 110. In other words, the first portion 110, the multiple first hooked and wound knots 140 and the second portion 120 are all woven by the same weaving filaments. The quantity of weaving filaments in each portion is equal, and each portion may be integrally woven. Therefore, although the weaving densities of the first portion 110 and the second portion 120 are different, the two portions do not need to be independently woven separately and then connected together. Even for woven bodies of the two portions with different integrated woven mesh densities, it also not necessary to remove part of the weaving filaments in adjacent woven bodies with larger woven mesh density for the purpose of forming sparser woven meshes at weaving intersections, thereby no weaving filament-removed ending portion will be formed at an intersection of the woven bodies of the two portions; thus, the phenomenon that the ending portion protrudes due to the blood-vessel dynamics or a curved blood vessel after the support is implanted is avoided, and the smooth consistency and the flexibility of the entire support are guaranteed.

After being hooked and wound, two weaving filaments constrict each other, thus reducing the freedom of movement. Particularly for continuous hooking and winding for multiple times in FIG. 3, two weaving filaments at a hooked and wound location cannot basically move relative to each other; when the endoluminal braided stent graft 100 is compressed into a sheath in a radial direction, the first hooked and wound knots 140 will not axially extend along with the radial compression of the endoluminal braided stent graft 100, so that the overall elongation of the endoluminal braided stent graft 100 is lowered. Correspondingly, when the endoluminal braided stent graft 100 is unfolded and released in the radial direction, if the second portion 120 is first attached to the lumen wall, the hooked and wound knots which are difficult to axially extend will suppress the release of the first portion 110 to not affect the second portion 120 which has already been attached, so as to prevent displacement of the released second portion 120 as much as possible, and the locating of the endoluminal braided stent graft 100 is facilitated to achieve a better treatment effect.

Figure 5:
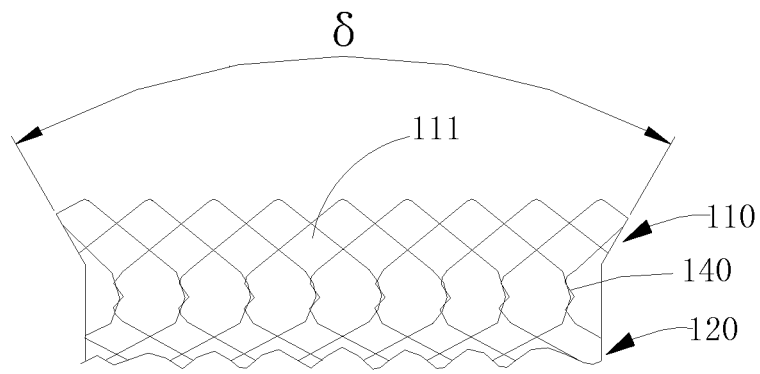
FIG. 5 is a partial structural schematic diagram of an endoluminal braided stent graft provided by a second embodiment of the present application.

FIG. 5 is a partial structural schematic diagram of an endoluminal braided stent graft provided by a second embodiment of the present application. Differences between the endoluminal braided stent graft provided by the second embodiment and the endoluminal braided stent graft provided by the first embodiment are as follows:

The first portion 110 includes a conical open end portion 111, and the radius length of the conical open end portion 111 is gradually increased from the side close to the second portion 120 to the side further away from the second portion 120. In other words, the conical open end portion 111 is of a horn shape. Particularly, the opening angle δ of the conical open end portion 111 is 45 to 120 degrees, and the opening angle here is a conical angle of an equivalent conical body of the conical opening end portion. During weaving, a conical mandrel with the opening angle δ may be adopted to form the conical opening portion 111.

The first portion 110 has the conical open end portion 111, so that after the first hooked and wound knots 140 are fixed, the weaving angle γ of the first portion 110 is larger in adjustment range and will not be limited by a weaving angle of the second portion 120. In addition, the conical open end portion 111 has an initial outward expansion tendency; when the endoluminal braided stent graft is radially compressed, the conical open end portion 111 has a larger outward expansion force. The horn-shaped structure is closely attached to a blood vessel wall in when radially expanded, thus further improving the anchoring property and the attachment property to the lumen, and avoiding the risk of displacement of the endoluminal braided stent graft.

Figure 6:
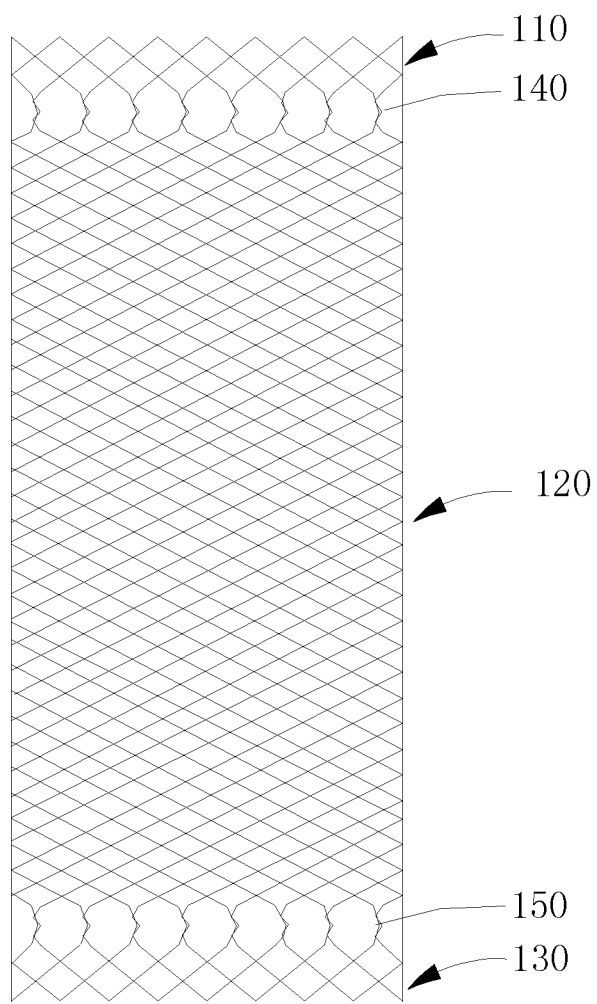
FIG. 6 is a structural schematic diagram of an endoluminal braided stent graft provided by a third embodiment of the present application.

FIG. 6 is a structural schematic diagram of an endoluminal braided stent graft provided by a third embodiment of the present application. Differences between the endoluminal braided stent graft provided by the third embodiment and the endoluminal braided stent graft provided by the first embodiment are as follows:

The meshed tubular body further includes a third portion 130 which is further away from the first portion 110 along the axial direction. The second portion 120 is connected with the third portion 130 through a plurality of second hooked and wound knots 150. The mesh density of the third portion 130 is different from that of the second portion 120. In another specific implementation mode, the mesh density of the first portion 110 is equal to that of the third portion 130.

The method of forming the first hooked and wound knots 140 is the same as that of the second hooked and wound knots 150; in other words, each second hooked and wound knot 150 may be formed by hooking and winding at least two weaving filaments once, or continuously hooking and winding at least two weaving filaments for multiple times. In addition, at least two weaving filaments from one end, which is close to the third portion 130, of the second portion 120 are hooked and wound to each other to form one second hooked and wound knot 150 and are then separated, and the weaving filaments of all the second hooked and wound knots 150 are woven to form the third portion 130. On one end side of the second portion 120, all the weaving filaments weaving the second portion 120 are used for forming the second hooked and wound knots 150, and all the weaving filaments constituting the second hooked and wound knots 150 are from the second portion 120, namely all the weaving filaments of the third portion 130 are from the second hooked and wound knots 150. Therefore, the second portion 120, the multiple second hooked and wound knots 150 and the third portion 130 are all woven by the same weaving filaments; and the quantity of the weaving filaments in each portion is equal, and these portions may be integrally woven. The first portion 110, the multiple first hooked and wound knots 140, the second portion 120, the multiple second hooked and wound knots 150 and the third portion 130 are all woven by the same weaving filaments; and the quantity of the weaving filaments in each portion is equal, and these portions may be integrally woven.

In this embodiment, the mesh density of the third portion 130 is smaller than that of the second portion 120; and if the third portion 130 includes an open end portion, such as an open distal end, the risk of restenosis of the open end portion is lowered. The open end portion of the third portion 130 is also of a horn shape, which is a conical open end portion. The mesh density of the third portion 130 can be larger than that of the second portion 120; in case of implantation into a bent lumen portion, the second portion 120 has a better flexibility due to its smaller mesh density, and at a smooth lumen portion, the third portion 130 can provide a greater radial supporting force to guarantee sufficient anchoring.

It is worth mentioning that the endoluminal braided stent graft in other implementation modes of the present application may include a plurality of the above-mentioned second portions. The multiple second portions are arrayed on the meshed tubular body in various ways, for example, the multiple second portions are arrayed in a spaced-apart manner along the axial direction, and every two adjacent second portions are connected through a plurality of hooked and wound knots. Similarly, the support further includes a plurality of the third portions, and their arraying methods are referred to the arraying methods of the multiple second portions, or the multiple section portions and the multiple third portions are alternately arrayed in a spaced-apart manner along the axial direction, and every two adjacent portions are connected through a plurality of hooked and wound knots. The above settings are merely regarded as illustrations, but are not to limit the present application. A person skilled in the art will select a proper structural combination according to a practical implantation requirement, and no further details will be described here.

All technical features of the above-mentioned embodiments may be randomly combined. In order to simplify the description, not all possible combinations of all the technical features in the above-mentioned embodiments are described. However, in case of no contradictions at all, the combinations of these technical features should be regarded as the scope specified in the specification.

The above-mentioned embodiments only show several implementation modes of the present application and their descriptions are more specific and detailed, but they are not limitations to the scope of the present application. It should be noted that a general person skilled in the art may further make multiple transformations and improvements without departing from the concept of the present application, and these transformations and improvements all fall within the scope of protection of the present application. Therefore, the scope of protection of the present application shall be based on the attached claims.

The invention claimed is:

1. An endoluminal braided stent graft, comprising:
a meshed tubular body woven by weaving filaments, wherein the meshed tubular body comprises a first portion and a second portion along an axial direction;
the meshed tubular body further comprises a plurality of first hooked and wound knots; at least two weaving filaments from one end of the second portion are hooked and wound to each other in the axial direction of the meshed tubular body to form one of the first hooked and wound knots and are then separated, and all the weaving filaments constituting the first hooked and wound knots are woven to form the first portion, and the mesh density of the first portion is smaller than that of the second portion; and
wherein the first portion comprises a conical open end portion, and the radius length of the conical open end portion is gradually increased from one side closer to the second portion to another side further away from the second portion.

2. The endoluminal braided stent graft according to claim 1, characterized in that an opening angle of the conical open end portion is 45 to 120 degrees.

3. The endoluminal braided stent graft according to claim 1, characterized in that at least two weaving filaments in each first hooked and wound knot are hooked and wound to each other once, or at least two weaving filaments in each first hooked and wound knot are continuously hooked and wound to each other at least twice; when the meshed tubular body comprises a plurality of second hooked and wound knots, two weaving filaments in each second hooked and wound knot are hooked and wound to each other once, or two weaving filaments in each second hooked and wound knot are continuously hooked and wound to each other at least twice.

4. The endoluminal braided stent graft according to claim 1, characterized in that the plurality of first hooked and wound knots are uniformly distributed in the circumferential direction of the meshed tubular body.

5. The endoluminal braided stent graft according to claim 1, characterized in that the meshed tubular body comprises a plurality of second portions which are spaced-apart in an arrayed manner along the axial direction, and every two adjacent second portions are connected with each other through the plurality of first hooked and wound knots.

6. The endoluminal braided stent graft according to claim 1, characterized in that the meshed tubular body further comprises a plurality of second hooked and wound knots and a third portion along the axial direction, and the third portion and the first portion are respectively located at two ends of the second portion; at least two weaving filaments from the other end of the second portion are hooked and wound to each other to form one of the second hooked and wound knots and are then separated; and the weaving filaments of all the second hooked and wound knots are woven to form the third portion.

7. The endoluminal braided stent graft according to claim 6, characterized in that the mesh density of the third portion is different from that of the second portion.

8. The endoluminal braided stent graft according to claim 6, characterized in that the plurality of second hooked and wound knots are uniformly distributed in the circumferential direction of the meshed tubular body.

9. The endoluminal braided stent graft according to claim 6, characterized in that the mesh density of the first portion is the same as that of the third portion.

10. The endoluminal braided stent graft according to claim 6, characterized in that the meshed tubular body comprises a plurality of third portions which are spaced-apart in arrayed manner along the axial direction, and every two adjacent third portions are connected with each other through the plurality of second hooked and wound knots.

* * * * *